(12) United States Patent
Konstandopoulos

(10) Patent No.: US 8,127,592 B2
(45) Date of Patent: *Mar. 6, 2012

(54) PARTICULATE MATTER DETECTION SENSOR

(75) Inventor: Athanasios G. Konstandopoulos, Salonika (GR)

(73) Assignees: Ibiden Co., Ltd., Ogaki-Shi (JP); Athanasios G. Konstandopoulos, Salonika (GR)

( * ) Notice: Subject to any disclaimer, the term of this patent is extended or adjusted under 35 U.S.C. 154(b) by 533 days.

This patent is subject to a terminal disclaimer.

(21) Appl. No.: 11/852,208

(22) Filed: Sep. 7, 2007

(65) Prior Publication Data

US 2008/0087007 A1   Apr. 17, 2008

(30) Foreign Application Priority Data

Oct. 17, 2006   (EP) ..................................... 06386034

(51) Int. Cl.
*G01F 1/34* (2006.01)
*G01M 15/10* (2006.01)

(52) U.S. Cl. ...................................... 73/28.03; 73/23.33

(58) Field of Classification Search ................... 73/23.2, 73/23.33, 28.01, 28.03, 38
See application file for complete search history.

(56) References Cited

U.S. PATENT DOCUMENTS

| | | | |
|---|---|---|---|
| 4,633,706 A * | 1/1987 | Ito et al. ....................... | 73/23.33 |
| 5,651,248 A | 7/1997 | Kawamura | |
| 5,822,977 A * | 10/1998 | Fukuda et al. .................. | 60/274 |
| 7,370,474 B2 * | 5/2008 | Minami .......................... | 60/295 |
| 7,658,064 B2 * | 2/2010 | Konstandopoulos ........... | 60/297 |
| 2005/0103013 A1 * | 5/2005 | Brookshire et al. .......... | 60/605.2 |
| 2005/0274104 A1 * | 12/2005 | Bromberg et al. .............. | 60/275 |
| 2008/0087011 A1 | 4/2008 | Konstandopoulos | |
| 2008/0087012 A1 | 4/2008 | Konstandopoulos | |
| 2008/0087101 A1 | 4/2008 | Konstandopoulos | |
| 2008/0098724 A1 | 5/2008 | Konstandopoulos | |

FOREIGN PATENT DOCUMENTS

| | | | |
|---|---|---|---|
| EP | 601287 A2 * | 6/1994 | |
| EP | 0 682 174 | 11/1995 | |
| EP | 0611962 | 4/1998 | |
| JP | 55-19934 | * 2/1980 | |
| JP | 60-242341 | * 12/1985 | |
| JP | 2005-240652 | * 9/2005 | |
| JP | 2006-226808 | 8/2006 | |
| WO | WO85/02883 | 7/1985 | |
| WO | WO 2004/031548 A1 * | 4/2004 | |
| WO | WO 2008043422 | 4/2008 | |

OTHER PUBLICATIONS

European Search Report, 06386034.0, mailed Mar. 9, 2007.
Japanese Office Action for corresponding JP Application No. 2007-209683, Jul. 19, 2011.

* cited by examiner

*Primary Examiner* — Daniel S Larkin
(74) *Attorney, Agent, or Firm* — Ditthavong Mori & Steiner, P.C.

(57) ABSTRACT

A particulate matter sensor includes a particulate matter detection filter having a volumetric soot storage capacity smaller than the volumetric soot storage capacity of a diesel particulate filter, and a differential pressure measuring part measuring a differential pressure between an inlet and an outlet of the particulate matter detection filter.

19 Claims, 15 Drawing Sheets

EXHAUST GAS

PARTICULATE MATTER DETECTION SENSOR

CROSS-REFERENCE TO RELATED APPLICATIONS

The present application claims priority under 35 U.S.C. §119 to European Patent Application No. 06386034.0 filed on Oct. 17, 2006. The contents of this European Patent application are incorporated herein by reference in their entirety.

BACKGROUND OF THE INVENTION

1. Field of the Invention

The present invention relates to a particulate matter detection sensor.

2. Discussion of the Background

Conventionally, a diesel particulate filter (DPF) of porous ceramic has been used for collecting particulate matter (PM) primarily of C (carbon) emitted from a diesel engine. With such a diesel particulate filter, there occurs gradual deposition of particulate matter with continual use thereof, and thus, it has been practiced in the art of exhaust gas purifying apparatus that uses a diesel particulate filter to remove the deposited particulate matter by causing a burning process inside the diesel particulate filter periodically and regenerate the diesel particulate filter.

It is preferable that such regeneration of the diesel particulate filter is conducted during the operation of the diesel engine, without replacing or dismounting the filter, and thus, it is practiced in the art to carry out fuel injection in the state that the piston is moving down in the cylinder following combustion to form a high temperature gas (post injection process). Thereby, the deposited particulate matter is burned with the high temperature gas thus formed.

FIG. 1 shows the overall construction of a conventional exhaust gas purifying system of a diesel engine equipped with a diesel particulate filter according to a related art of the present invention.

With the conventional exhaust gas purifying system explained with reference to FIG. 1, it should be noted that such regeneration of the filter is conducted each time the vehicle has traveled a predetermined mileage such as 500 km, over the duration of 10 minutes, for example.

In the case the filter regeneration by way of post injection has been conducted impartially, the regeneration is carried out irrespective of an actual amount of collection of the particulate matter in the filter. Thus, in order to ensure that there occurs no excessive deposition of the particulate matter in the filter, there is a need to set the interval of filter regeneration to be shorter than what is actually needed for the sake of safety.

U.S. Pat. No. 5,651,248 describes the construction that uses, in addition to the diesel particulate filter, a detection filter and evaluates the amount of the particulate matter collected in the detection filter by measuring the electric resistance. According to this technology, the particulate matter collected by the diesel particulate filter and the particulate matter collected by the detection filter are subjected to burning by using a heater when the detected resistance has decreased below a predetermined value. With this, regeneration of filter is achieved.

The contents of U.S. Pat. No. 5,651,248 are incorporated by reference in their entirety.

SUMMARY OF THE INVENTION

The present invention provides a particulate matter sensor including: a particulate matter detection filter having a soot storage capacity smaller than the soot storage capacity of a diesel particulate filter; and a differential pressure measuring part measuring a differential pressure between an inlet and an outlet of the particulate matter detection filter.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
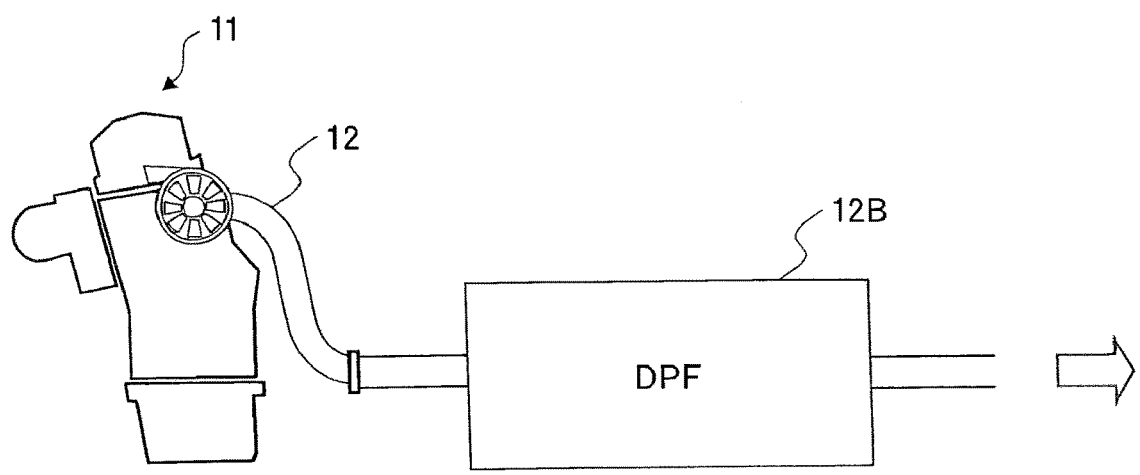
FIG. 1 is a diagram showing an overall engine system that uses a conventional exhaust gas purifying apparatus.

The embodiments will now be described with reference to the accompanying drawings, wherein like reference numerals designate corresponding or identical elements throughout the various drawings.

According to an embodiment of the present invention, there is provided a particulate matter detection sensor, including: a particulate matter detection filter having a volumetric soot storage capacity smaller than the volumetric soot storage capacity of a diesel particulate filter; and a differential pressure measuring part measuring a differential pressure between an inlet and an outlet of the particulate matter detection filter.

Preferably, the particulate matter detection sensor further includes a flow meter or equivalent meter (e.g. a gas velocity meter).

Preferably, the particulate matter detection sensor further includes a temperature measuring part.

Preferably, the particulate matter detection sensor further includes a heater.

Preferably, the particulate matter detection sensor further includes a vessel, wherein at least one of the particulate matter detection filter, the differential pressure measuring part, the temperature measuring part or the flow meter or equivalent meter (e.g. a gas velocity meter) is accommodated into the vessel.

Preferably, the particulate detection filter includes any of SiC, aluminum nitride, silicon carbide, boron nitride, tungsten nitride, zirconium carbide, titanium carbide, tantalum carbide, tungsten carbide, alumina, zirconium oxide, cordierite, mullite, silica, or aluminum titanate.

Hereinafter, preferred embodiments of the present invention will be described with reference to the drawings.

Referring to FIG. 1, a diesel engine 11 has an exhaust line 12, wherein there is provided a diesel particulate filter 12B in the exhaust line 12 for collecting the particulate matter contained in the exhaust gas and emitted from the diesel engine 11.

Figure 2A:
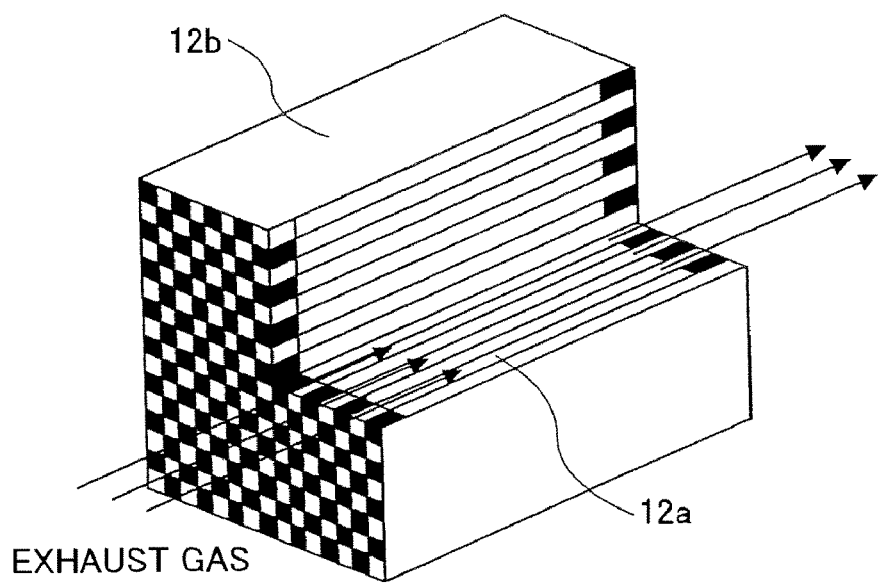
FIG. 2A is a diagram showing a schematic construction of a constituent element of a diesel particulate filter.
Figure 2B:
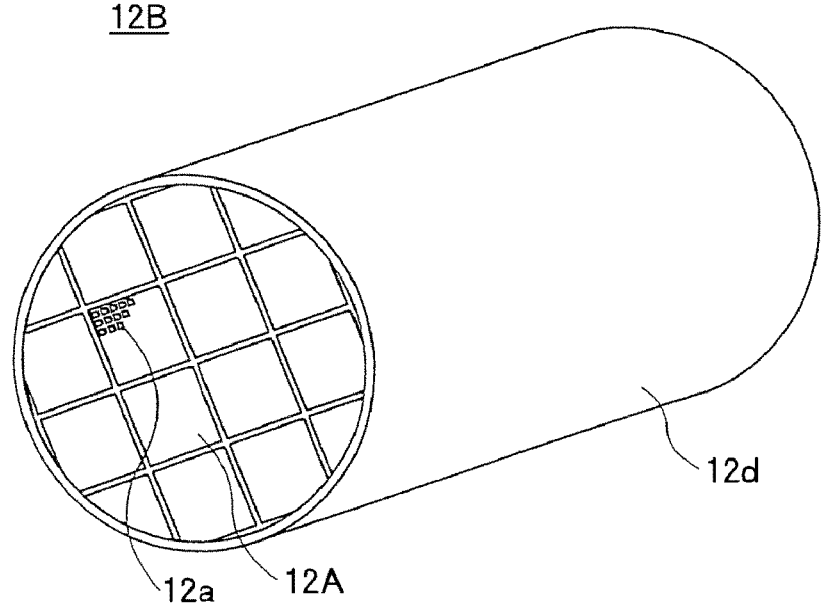
FIG. 2B is a diagram showing the diesel particulate filter.

FIG. 2B shows the outline of the diesel particulate filter 12B while FIG. 2A shows an element that constitutes the diesel particulate filter.

The diesel particulate filter 12B is formed of a filter unit 12A of a porous ceramic, typically of SiC, wherein there are formed a large number of gas passages 12a in the filter unit 12A so as to extend from one end to the other end thereof with a cross-section of 1 mm×1 mm, for example.

Thereby, the diesel particulate filter 12B is formed by binding plural filter units (filter elements) 12A by a seal material (adhesion layer) and machining the peripheral part thereof such that the filter 12B as a whole has a cylindrical form. Further, the peripheral surface of the filter 12B is covered by a seal material (coating layer) 12d. There may be a case in which only one unit 12A is used in the diesel particulate filter 12B.

Figure 2C:
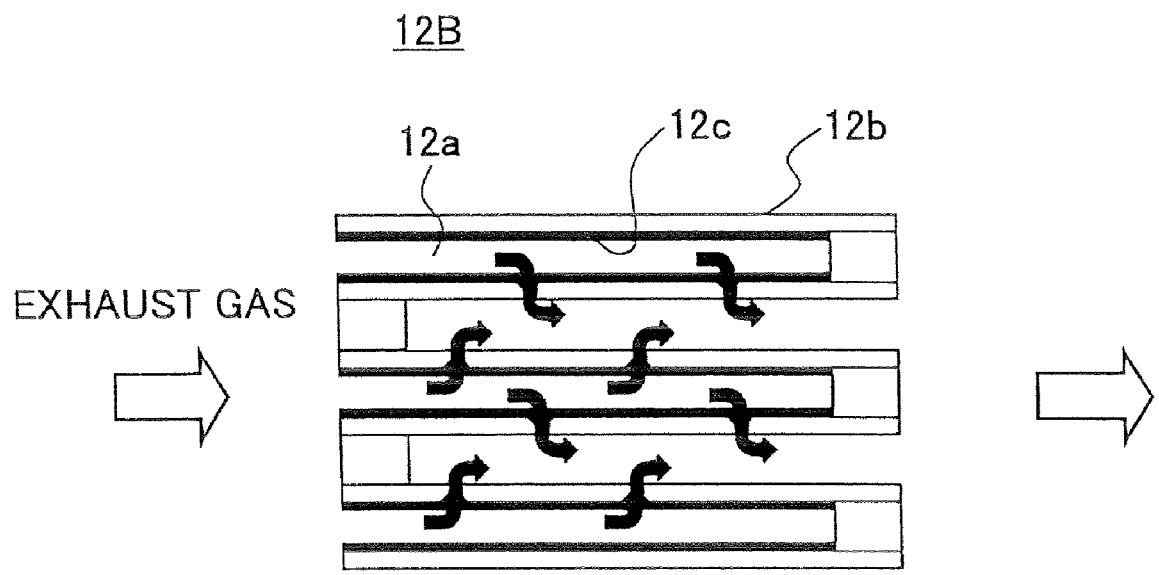
FIG. 2C is a diagram showing the operational principle of the diesel particulate filter.

FIG. 2C shows the principle of the diesel particulate filter 12B.

Figure 2D:
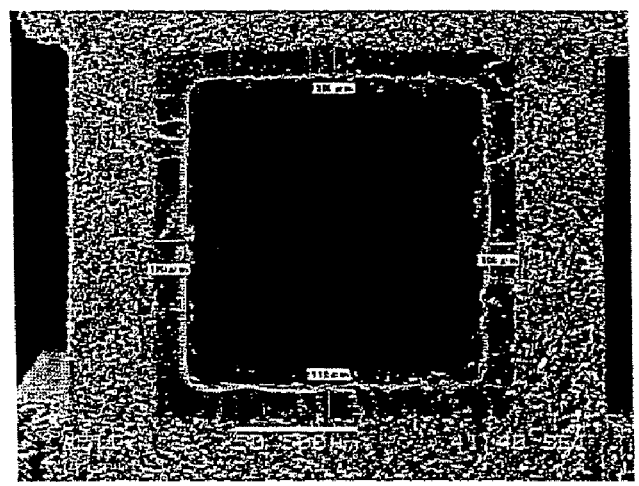
FIG. 2D is a diagram showing the state of the particulate matter collected by the diesel particulate filter.

As shown schematically in FIG. 2C, the plural gas passages 12a have their upstream ends or downstream ends closed alternately with regard to the direction of the exhaust gas flow from the engine, and the exhaust gas introduced to one such gas passage 12a passes to an adjacent gas passage by way of penetration through the porous member 12b of the filter 12B. Thereby, the particulate matter contained in the exhaust gas is collected by the porous member 12b as the exhaust gas penetrates therethrough, and there is caused deposition of the particulate matter 12c on the porous member 12b in the form of layer as shown in FIG. 2D.

Because the diesel particulate filter 12B thus causes deposition of the particulate matter contained in the exhaust gas therein, there is a need of regenerating the filter with suitable timing by conducting a regeneration process (burning of the deposited particulate matter), as described previously.

On the other hand, this U.S. Pat. No. 5,651,248 has a drawback in that, in addition to the problem that the construction thereof becomes complex because of the need of providing a heater in the diesel particulate filter, there occurs electric power consumption at the time of regeneration of the diesel particulate filter. In order to save the electric power consumption at the time of filter regeneration, the technology of U.S. Pat. No. 5,651,248 selects the timing of executing the filter regeneration such that the regeneration operation is conducted at the time the temperature of the diesel particulate filter is higher than a predetermined temperature, except for the case in which the diesel particulate filter is in the critical state with regard to the deposition of the particulate matter and it is inevitable to carry out regeneration immediately. As a result, there is imposed a restriction on the timing of the regenerating operation of the detection filter used for particulate detection with this technology, and the degree of freedom of regenerating operation of the particulate detection filter is restricted.

Further, with the technology of the U.S. Pat. No. 5,651,248, it is not possible to use the diesel particulate filter during the regeneration operation carried out by the heater, and because of this, there is provided a reserve diesel particulate filter and switches to this reserve diesel particulate filter during the regeneration process. However, such a construction requires two equivalent diesel particulate filters together with a switching valve, and there arises a problem in that the construction of the exhaust gas purifying apparatus becomes bulky. It is difficult to mount such an exhaust gas purifying apparatus on compact vehicles.

Further, with the technology of the U.S. Pat. No. 5,651,248, regeneration of the detection filter is carried out concurrently with the diesel particulate filter or consecutively to the diesel particulate filter, while such a construction cannot choose the timing of regeneration of the detection filter arbitrarily, and there is a problem that error tends to be caused in the regeneration timing of the diesel particulate filter, depending upon the state of the detection filter.

When regeneration of the diesel particulate filter and regeneration of the detection filter are carried out independently, there is caused a decrease of ventilation resistance in the detection filter upon regeneration thereof, and the exhaust gas starts to flow primarily through the detection filter. Thereby, there is caused an error in the detection of regeneration timing of the diesel particulate filter. From these reasons, the technology of U.S. Pat. No. 5,651,248 carries out the regeneration of the detection filter and the regeneration of the diesel particulate filter in synchronization as explained before.

Further, the technology of the U.S. Pat. No. 5,651,248 has a drawback in the points of: (a) ash deposition; and (b) large evaluation error caused by deterioration.

Further, with the technology of the U.S. Pat. No. 5,651,248, there arises another problem from the very principle thereof of measuring electric resistance of electrode for evaluating the deposition amount of the collected particulate matter.

Figure 3:
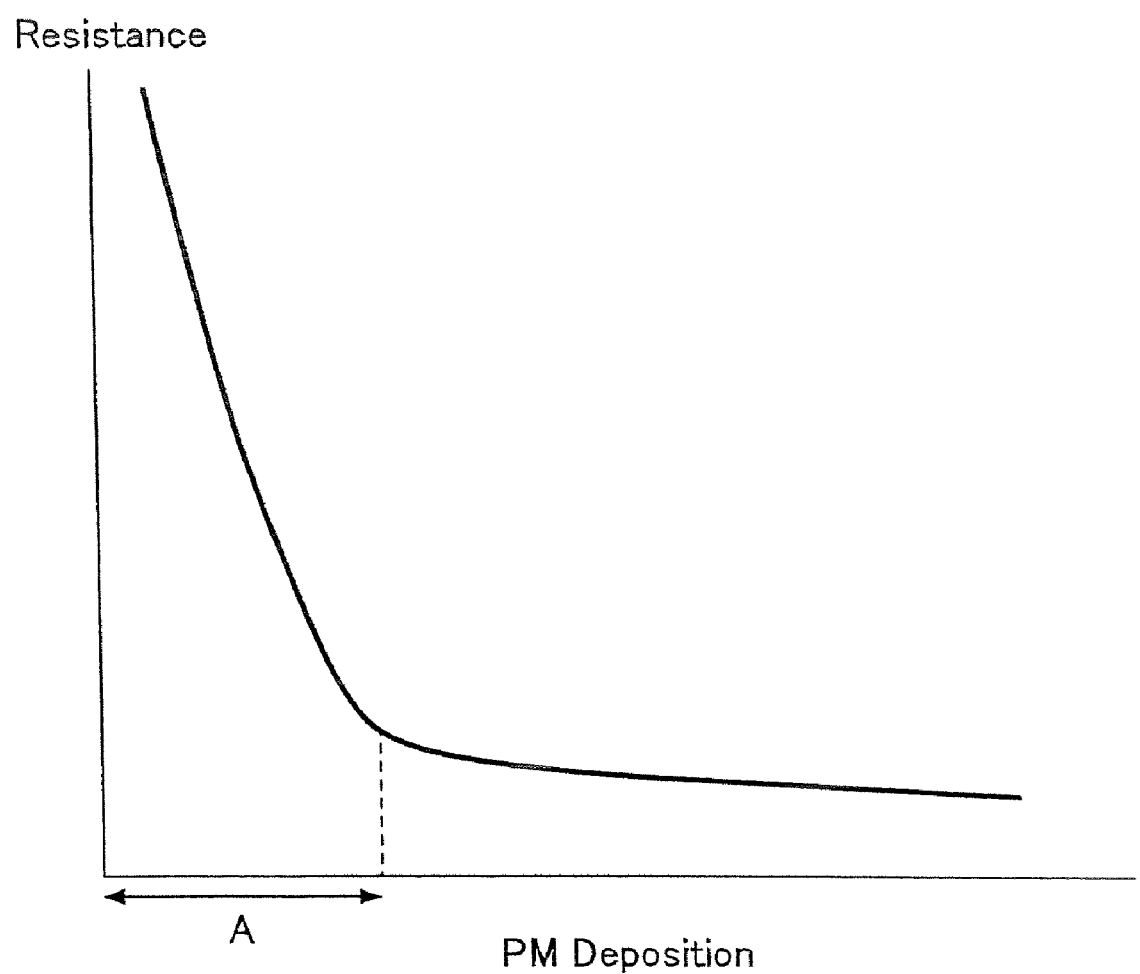
FIG. 3 is a diagram explaining the problems in conventional art.

However, there generally exists a non-linear relationship between the deposition amount of the particulate matter collected by the detection filter and the electric resistance thereof as shown in FIG. 3, and it is necessary to use the linear region designated in FIG. 3 by "A" in order to obtain the deposition amount of the particulate matter precisely.

In order to use such a linear region, however, there is a need of maintaining small deposition amount in the detection filter, while this means that frequent regeneration of detection filter is needed. With the technology of the U.S. Pat. No. 5,651,248, however, the timing of regeneration is restricted for the detection filter, and thus, there inevitably arises the problem that the accuracy of evaluation of the particulate matter deposition amount is degraded. When regeneration of the detection filter is forced under such a situation, not only the electric power consumption is increased but there is also caused a detachment between the state of the detection filter and the state of the diesel particulate filter, and there is caused an error in the regeneration timing of the diesel particulate filter.

Further, in the case there is caused a deposition of ash in the diesel particulate filter or detection filter after burning of the particulate matter, no precise measurement of electrical resistance is possible anymore and there should be caused a large error in the evaluation of the deposition amount.

Further, with the use of the detection filter, there is caused degradation in the filter or electrode with time or with use in the ambient of exhaust gas. Particularly, the electrode (terminal formed of a conductive metal) is formed by infiltrating a metal such as Cu, Cr, Ni, or the like, and thus, there is a tendency of causing problems of physical degradation, oxidation degradation and thermal degradation, such as oxidation, adhesion of impurities, cracking, corrosion, and the like.

When there is caused degradation in the filter or electrode, it is no longer possible to carry out precise measurement of the electric resistance and errors tend to be caused in the evaluation of the deposition amount of the particulate matter.

According to the embodiment of the present invention, it becomes possible to measure the deposition amount of particulate matter in the primary diesel particulate filter simply and easily, by using a particulate detection filter provided in a gas line branched from an exhaust line of a diesel engine at an upstream side of a diesel particulate filter provided to the exhaust line, and particularly by using a particulate matter (PM) detection filter of small volumetric capacity and hence less prone to cause non-uniform deposition of the particulate matter, by measuring the differential pressure occurring in such a particulate matter detection filter. Thereby, it becomes possible to suppress deterioration of fuel efficiency by excessive post injection by using such a particulate matter detection sensor for the exhaust gas purifying apparatus. Further, with the embodiment of the present invention, it becomes possible to execute the regeneration of the particulate matter detection filter independently to the regeneration of the primary diesel particulate filter, and it becomes possible to constantly and precisely measure the deposition amount of the particulate matter in the primary diesel particulate filter by using the secondary diesel particulate filter. Further, it becomes possible to perform precise measurements while eliminating the effect of ash deposition or degradation of the filter or electrode.

Further, with the embodiment of the present invention, it becomes possible to avoid the problem of concentration of the exhaust gas of the exhaust line 21 to the gas line with regeneration of the particulate detection filter, which problem may be caused as a result of decrease of ventilation resistance of the gas line with regeneration of the particulate matter (PM) detection filter, by providing a valve in the gas line and controlling the flow rate therein to be constant. Thus, collection of the particulate matter in the primary diesel particulate filter is caused similarly to the particulate matter (PM) detection filter, and the deviation caused between the evaluation of the deposition amount of the particulate matter in the primary diesel particulate filter, carried out by the measurement of differential pressure in the particulate matter (PM) detection filter, and the actual deposition amount of the particulate matter in the primary diesel particulate filter, is effectively avoided.

First Embodiment

Figure 4:
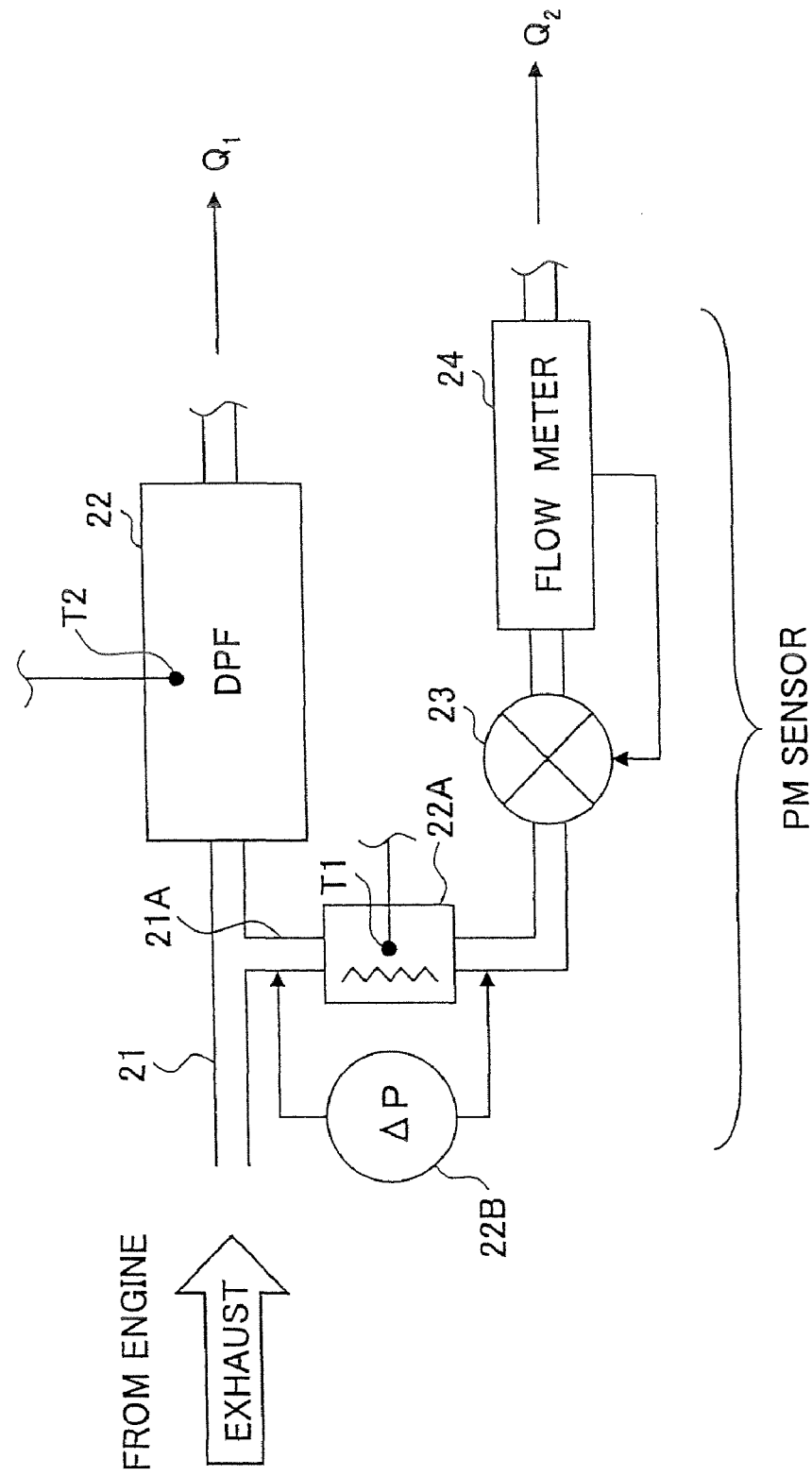
FIG. 4 is a diagram showing the construction of an exhaust gas purifying apparatus according to a first embodiment of the present invention.

FIG. 4 shows the construction of an exhaust gas purifying apparatus according to a first embodiment of the present invention.

Referring to the embodiment of FIG. 4, an exhaust gas from a diesel engine (not illustrated) is caused to flow into a primary diesel particulate filter (DPF) 22 similar to the one explained previously with reference to FIG. 2A via an exhaust line 21, and the primary diesel particulate filter (DPF) 22 collects the particulate matter in the exhaust gas as explained with reference to FIGS. 2C and 2D.

Further, with the construction of the embodiment of FIG. 4, a secondary exhaust line 21A is branched from the exhaust line 21 from an upstream side of the primary diesel particulate filter (DPF) 22, and a secondary diesel particulate filter 22A is provided to the secondary exhaust line 21A with a volume smaller than the volume of the primary diesel particulate filter (DPF) 22. Further, there is provided a differential pressure measuring part 22B for measuring a differential pressure $\Delta P$ caused between an inlet and an outlet of the secondary diesel particulate filter 22A. Further, with the construction of the embodiment of FIG. 4, there are provided a flow meter 24 and a control valve 23 in the secondary exhaust line 21A at a downstream side of the secondary diesel particulate filter 22A, wherein the control valve 23 is used for maintaining the flow rate of the exhaust gas in the secondary exhaust line 21A constant based on the measurement made by the flow meter 24. It should be noted that the control valve 23 and the flow meter 24 may be provided anywhere on the secondary exhaust line 21A. Here, it should be noted that the secondary diesel particulate filter 22A, the differential pressure measuring part 22B and the flow meter 24 constitutes together a particulate matter (PM) sensor that measures the amount of particulate contained in the exhaust gas. The particulate matter (PM) sensor noted above may or may not include the flow meter 24. The particulate matter (PM) sensor may be defined to include a temperature measuring part (T1). Further, it is possible to provide a temperature measurement part T2 in the primary diesel particulate filter (DPF) 22.

It should be noted that the temperature measuring part in the exhaust line may be provided in any of: (1) interior of the primary diesel particulate filter, (2) interior of the secondary diesel particulate filter, (3) in a pipe connected thereto, (4) exterior of the primary diesel particulate filter, or (5) exterior of the secondary diesel particulate filter. From the viewpoint of precise measurement of the exhaust gas temperature, the arrangement of (1) or (2) is preferable, wherein the arrangement of (2) is thought more preferable.

In the embodiment of FIG. 4, the primary diesel particulate filter (DPF) 22 is formed of a porous ceramic of SiC, or the like having a porosity of about 35% to about 65% in the form of a honeycomb structure, wherein it can be seen that there are formed gas passages of a rectangular cross-section having a length of 1.1 mm, for example, for each edge in the cross-section taken perpendicular to the gas flow direction, in correspondence to the gas passages 12a of FIG. 2B, wherein the gas passages are arranged with a mutual separation of about 0.3 mm and form together a lattice pattern.

Here, it should be noted that, in the present invention, the particulate matter (PM) detection filter is called also a secondary diesel particulate filter.

As shown in FIG. 4, the particulate matter detection sensor of the present embodiment is formed by the secondary exhaust line 21A, the secondary diesel particulate filter 22A and the differential pressure measuring part 22B measuring the differential pressure $\Delta P$ between the inlet and outlet of the secondary diesel particulate filter 22A. Therein, it will be noted that "particulate matter sensor" is defined as the part performing the function of particulate detection (constituting elements realizing the function of particulate matter detection).

Thus, with the particulate matter sensor of the present embodiment, the constituent elements of the particulate matter detection function may be provided in the form connected by pipes or in the form of an integral unit accommodating in a holder 22e, for example, or in a metal housing.

Further, as shown in the embodiment of FIG. 4, it is possible that the particulate matter sensor includes the control valve 23 or flow meter 24 in the form connected by pipes. Alternatively, the control valve 23 and the flow meter 24 may be integrated to the particulate matter sensor. Further, the particulate matter sensor may include the temperature measuring part T1.

In the case the temperature measuring part T2 is used for measurement of temperature of the exhaust gas in place of the temperature measuring part T1, the particulate matter sensor includes also the temperature measuring part T2.

Figure 5A:
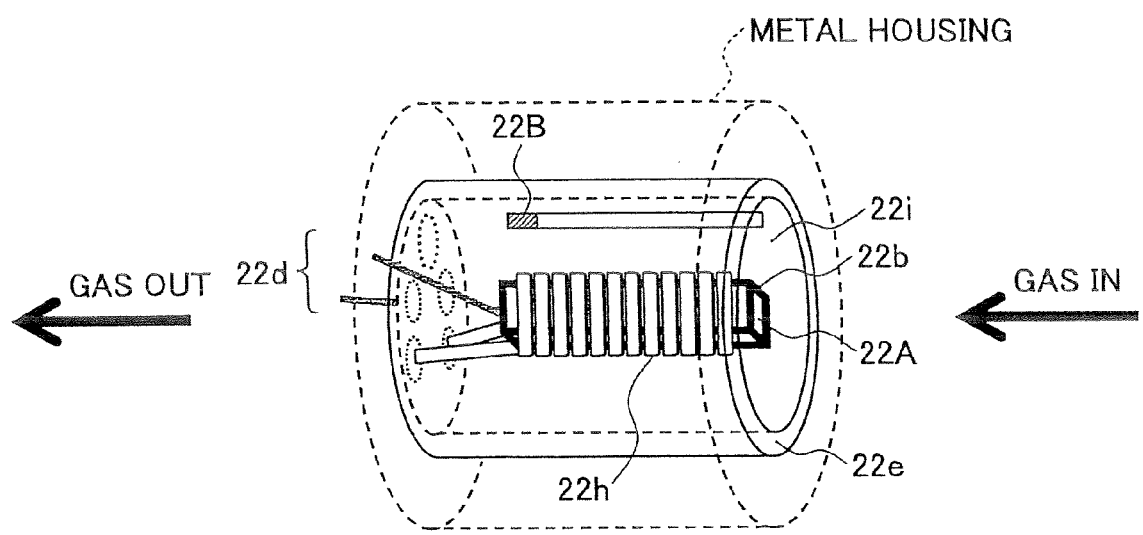
FIG. 5A is a diagram showing the construction of a secondary diesel particulate filter used in FIG. 4.
Figure 5B:
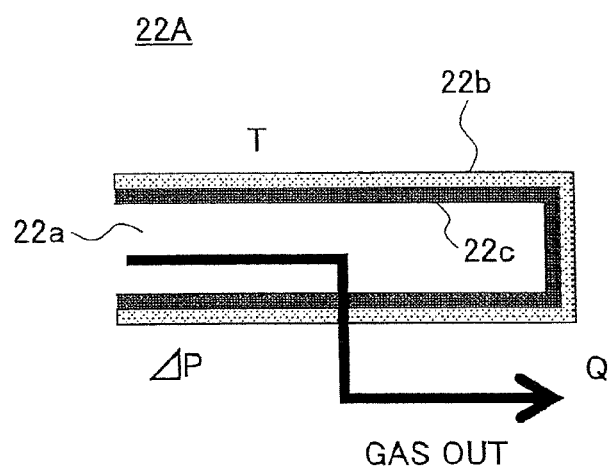
FIG. 5B is a diagram explaining the principle of the secondary diesel particulate filter of FIG. 5A.

FIG. 5A shows the overall construction including the secondary diesel particulate filter 22A, while FIG. 5B shows the principle of the secondary diesel particulate filter 22A.

It should be noted that the secondary diesel particulate filter 22A may be formed of a porous ceramic similar to the primary diesel particulate filter (DPF) 22. In the case the secondary diesel particulate filter is formed of a porous ceramic, it is preferable that the secondary diesel particulate filter includes a cell 22b of a rectangular form. Therein, there is formed a single gas passage 22a having a volume of about 65 ml or less such as about 0.05 to about 65 ml, or about 5% or less such as about 0.05 to about 5% of the total volume of the exhaust gas passages (corresponding to passage 12a of FIG. 3) in the primary diesel particulate filter (DPF) 22. Alternatively, the gas passage 22a may have a filtration area of about 0.1 to about 1000 cm$^2$ (preferably about 1 to about 10 cm$^2$). The gas passage 22a may have a rectangular cross-sectional shape, for example, and is formed in the state that one end thereof is closed (rear end is closed in the case of a cell). Here, it should be noted that the outer shape of the gas passage 22a or the outer shape of the secondary diesel particulate filter 22A (cell 22b) is not necessarily identical to the cross-sectional shape of the gas passages of the primary diesel particulate filter (DPF) 22, and thus, they can be shaped to any arbitrary shape of circular, square, octahedral, elliptical, or the like. Further, it should be noted that the porous ceramic constituting the secondary diesel particulate filter 22A (cell 22b) is not necessarily identical with the porous ceramic that forms the primary diesel particular filter (DPF) 22. Further, it should be noted that the secondary diesel particulate filter 22A (cell 22b) may be formed of a material other than ceramics.

By forming the gas passage 22a with the volume of about 5% or less of the exhaust gas passage (corresponds to the passage 12a of FIG. 3) in the primary diesel particulate filter (DPF) 22, or with the volume of 65 ml or less, or with the filtration area of about 0.1 to about 1000 cm$^2$ (preferably about 1 to about 10 cm$^2$), it becomes possible to measure the deposition amount of the particulate matter in the primary diesel particulate filter (DPF) 22 with a simple procedure.

The secondary diesel particulate filter 22A (cell 22b) is provided with a temperature measuring part for measuring the exhaust gas temperature T, and a thermocouple 22d is provided for the temperature measuring part. Further, a heater 22h is wound around the secondary diesel particulate filter (cell 22b) for incinerating a soot layer 22c deposited on the inner wall surface and regenerating the secondary diesel particulate filter 22A. Further, the cell 22b, the thermocouple 22d and the heater 22h are accommodated in a cylindrical holder 22e of $SiO_2$—$Al_2O_3$, or the like, by interposing an insulator 22i of $Al_2O_3$, or the like, and there is provided a diaphragm pressure gauge 22B in the holder 22e for measuring the differential pressure ΔP, in such a manner that the exhaust gas in the secondary exhaust line 21A is supplied to the pressure gauge 22B. The holder 22e is accommodated in a metal housing and is provided to the secondary exhaust line as the particulate matter (PM) sensor. The holder 22e may also be provided inside the pipe of the secondary exhaust line or may be provided inside the secondary exhaust line in the state accommodated in the metal housing.

Thus, when the exhaust gas in the secondary exhaust line 21A is introduced to the exhaust passage 22a of the secondary diesel particulate filter (cell 22b), the exhaust is caused to flow outside the cell through the wall surface of the secondary diesel particulate filter (cell 22b), and the particulate matter in the exhaust gas is collected similarly to the case of FIG. 2C. Thereby, the particulate matter deposits on the inner surface of the cell 22b to form a layer 22c.

With the present embodiment, the deposition amount of the particulate 22c thus collected and deposited on the inner wall surface of the diesel particulate filter 22 is calculated from the pressure difference ΔP and the exhaust gas temperature T and exhaust gas flow rate Q thus obtained by using the equation (1) below.

Figure 6:
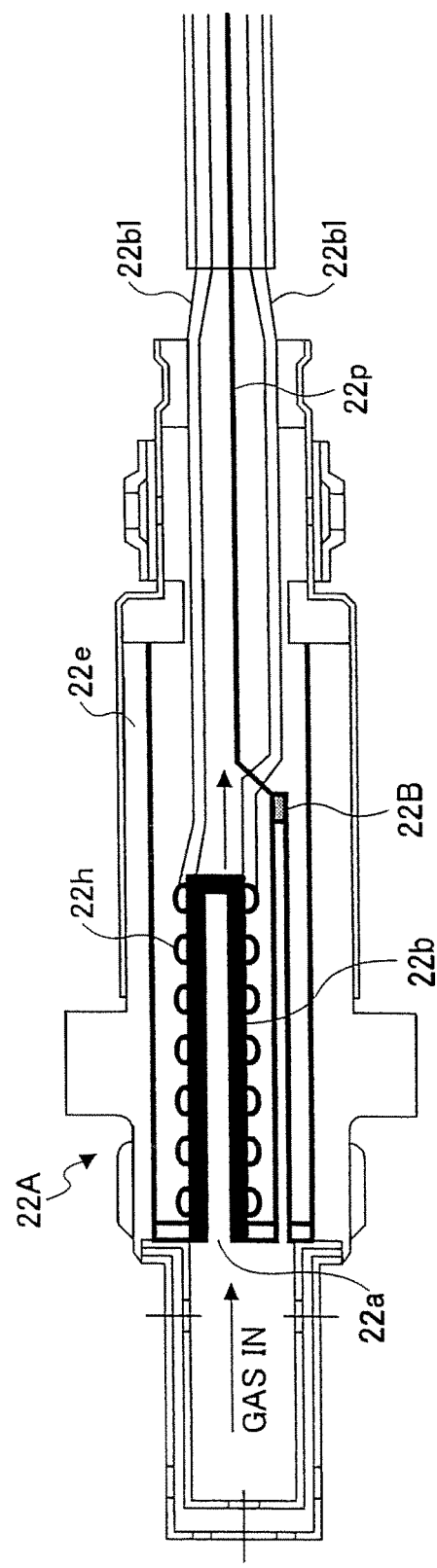
FIG. 6 is a diagram showing the construction of a particulate matter (PM) sensor that uses the secondary diesel particulate filter of FIG. 4.

FIG. 6 shows a more detailed construction of the secondary diesel particulate filter 22A of FIG. 4.

Referring to FIG. 6, the exhaust gas in the secondary exhaust line 21A is supplied to the gas passage 22a in the secondary diesel particulate filter (cell 22b) as represented by an arrow and is discharged, after passing through the cell, in the lateral direction or rear direction. Thereby, the heater 22h on the secondary diesel particulate filter (cell 22b) is driven by the electric power supplied by a drive line 22b1 and causes incineration in the particulate matter 22c collected by the cell 22b. Further, the output signal of the diaphragm pressure gauge 22B is supplied to a control circuit via a signal line 22p.

With the secondary diesel particulate filter 22A of FIGS. 5A and 5B, the amount of soot load of the particulate matter collected in the secondary diesel particulate filter is calculated according to an equation of the form
ΔP=function (Flow, Temperature, Soot load, Geometry)
with a preferred example shown below (although other expressions can be also employed) according to which the thickness W[m] of a layer 22c of the particulate matter collected in the secondary diesel particulate filter is calculated according to $$\Delta P = \frac{\mu Q}{2V_{trap}}(\alpha + W_s)^2 \left[ \frac{W_s}{K_w \alpha} + \frac{1}{2K_{SOOT}} \ln\left(\frac{\alpha}{\alpha - 2W}\right) + \frac{4FL^2}{3}\left(\frac{1}{(\alpha - 2W)^4} + \frac{1}{\alpha^4}\right) \right] + \frac{\rho Q^2 (\alpha + W_s)^4}{V_{trap}^2}\left[\frac{\beta W_s}{4} + 2\zeta\left[\frac{L}{\alpha}\right]^2\right] \quad (1)$$

wherein ΔP represents the differential pressure [Pa], μ represents a kinetic viscosity coefficient, Q represents the flow rate of the exhaust gas represented in terms of [m$^3$/h], α represents an edge length of the cell, ρ represents a specific gravity of the exhaust gas, $V_{trap}$ represents a filter volume, Ws represents a wall thickness, Kw represents a wall gas permeability, $K_{soot}$ represents a gas permeability of the collected particulate matter layer, W represents the thickness of the collected particulate matter layer, F is a numerical coefficient (=28.454), L represents an effective filter length, β represents the Forchheimer coefficient of the porous wall, ç represents the inertial loss coefficient of the exhaust gas entering and exiting the filter.

Next, the mass $m_{soot}$ of the particulate matter collected by the secondary diesel particulate filter (cell 21b) is obtained according to $$W = \frac{\alpha - \sqrt{\alpha^2 - \frac{m_{soot}}{N_{cells} \times L \times \rho_{soot}}}}{2} \quad (2)$$

wherein $m_{soot}$ represents the mass [g] of the particulate matter collected, while $N_{cells}$ represents an aperture number of the cell at the inlet side, and $\rho_{soot}$ represents the density of the collected particulate matter.

Thus, a collection amount per unit time, PM [g/h] is obtained by dividing $m_{soot}$ by the time [h] as measured from the previous regeneration of the secondary diesel particulate filter 22A.

Once the mass PM [g/h] of the particulate matter deposited in a unit time is obtained, the concentration of the particulate matter in the exhaust gas, $PM_{conc}$ [g/m³], is obtained by using the flow rate Q2 [m³/h] of the exhaust gas passing through the secondary diesel particulate filter 22A as $$PM[g/h]=PM_{conc}[g/m^3]\times Q2[m^3/h]. \quad (3)$$

Because the concentration $PM_{conc}$ of the particulate matter in the exhaust gas takes the same value in the secondary exhaust line 21A and also in the exhaust lien 21, the amount of the particulate matter $PM_{enter\,full\,filter}$ [g/h] that has flowed into the diesel particulate filter 22 is obtained from the mass PM [g/h] of the particulate matter deposited per unit time, as $$PM_{enter\,full\,filter}[g/h]=PM_{conc}[g/m^3]\times Q1[m^3/h] \quad (4)$$

Further, from this, the amount of the particulate matter deposited in the filter is obtained by taking into consideration the collection efficiency of the filter. In the foregoing, Q1 represents the flow rate of the exhaust gas passing through the primary diesel particulate filter (DPF) 22. Q1 may be obtained by actual measurement or estimated from the operational state of the engine.

Figure 7:
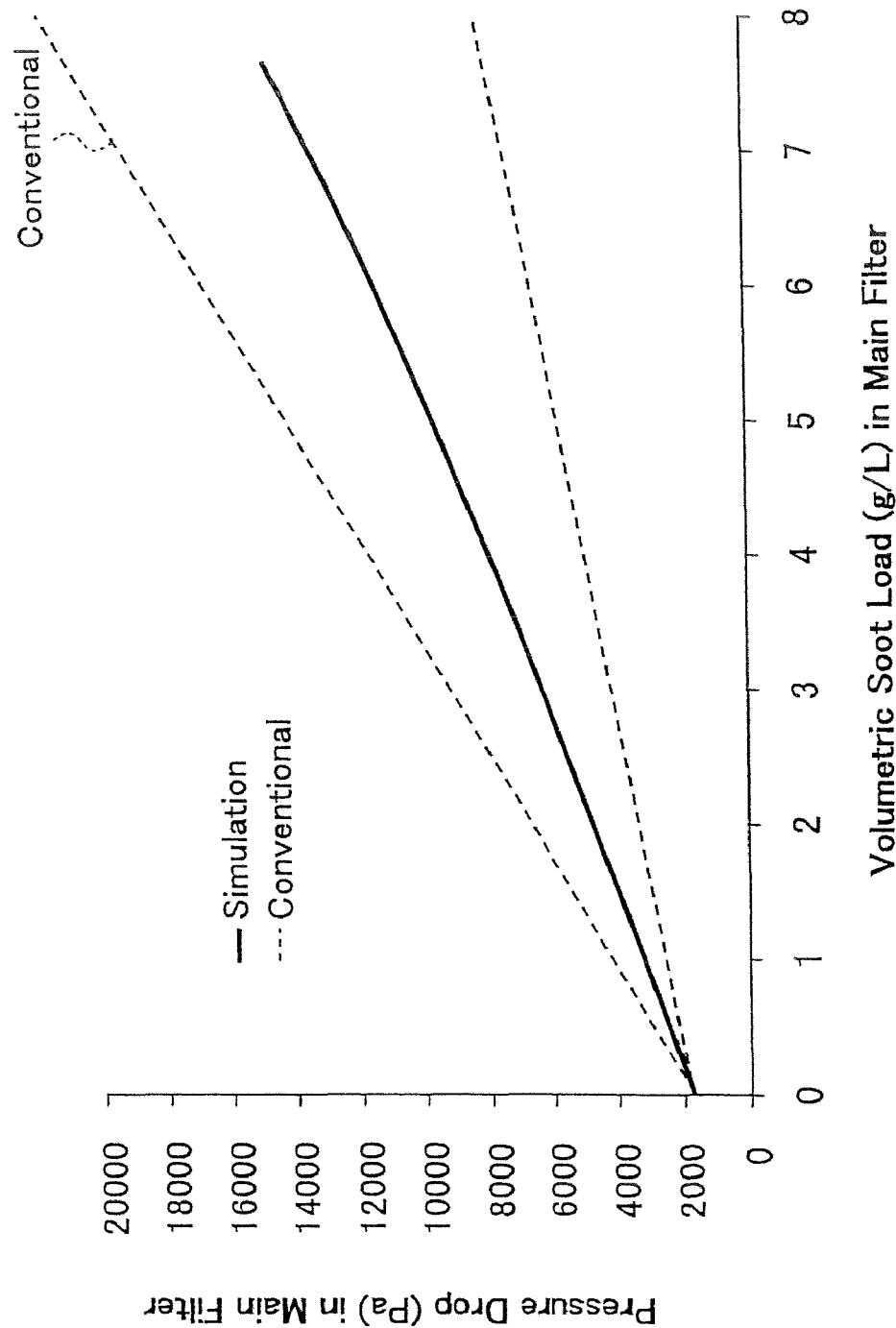
FIG. 7 is a diagram explaining the effect of the embodiment of the invention.

FIG. 7 shows the relationship between the differential pressure occurring across the primary diesel particulate filter (DPF) 22 of the exhaust gas purifying apparatus of the embodiment of FIG. 4 and the deposition amount of the particulate matter in the primary diesel particulate filter (DPF) 22, wherein it should be noted that the continuous line shows the case in which the deposition amount of the particulate matter in the main diesel particulate filter 22 is obtained by using the secondary diesel particulate filter 22A and Equations (1) to (4). On the other hand, the dotted line represents the case in which the deposition amount of the particulate matter in the primary diesel particulate filter (DPF) 22 is obtained directly from the differential pressure across the primary diesel particulate filter (DPF) 22.

Referring to FIG. 7, it can be seen that there can occur a variation, and hence error, of as much as about ±50% in the differential pressure across the primary diesel particulate filter (DPF) 22 when compared at the same deposition amount of the particulate matter.

Contrary to this, it is possible to obtain the amount of deposition of the particulate matter collected by the primary diesel particulate filter (DPF) 22 within the error of about ±10% by obtaining the differential pressure ΔP across the secondary diesel particulate matter and by using Equations (1) to (4).

Thus, according to the embodiment of the present invention, it becomes possible to evaluate the deposition amount of the particulate matter in the primary diesel particulate filter (DPF) 22 in the exhaust gas purifying apparatus of the embodiment of FIG. 4 precisely by measuring the differential pressure ΔP formed in the secondary diesel particulate filter 22A of small volume, and it becomes possible to execute the regeneration of the primary diesel particulate filter (DPF) 22 with optimum timing by way of carrying out the post injection based on the foregoing result. With this, unnecessary post injection is avoided and the fuel efficiency of the vehicle is improved.

In the construction of the embodiment of FIG. 4, it is possible to use a known Vencheri flow meter or hotwire flow meter, wherein the flow meter 24 can control the exhaust gas flow rate in the secondary exhaust line 21A generally constant within the range of about 50 to about 6000 ml/min, for example. With this, one-sided flow of the exhaust gas through the secondary exhaust line 21A is avoided, and it becomes possible to obtain the deposition amount of the particulate matter in the primary diesel particulate filter (DPF) 22 from the deposition amount obtained by using the secondary diesel particulate filter 22A, with further improved precision.

Here, it should be noted that the "differential pressure measuring part measuring a differential pressure between an inlet and an outlet of said secondary diesel particulate filter" includes not only the differential pressure measuring part that measures the differential pressure between the inlet side and the outlet side of the secondary diesel particulate filter 22A but also the construction that uses a pressure gauge only at the outlet side of the diesel particulate filter 22A. With such a construction, the pressure value of the initial state (the state immediately after regeneration) is memorized and the differential pressure is calculated by measuring the pressure for the state in which there occurred deposition of the particulate material in the secondary diesel particulate filter 22A and by subtracting the pressure value thus obtained from the memorized initial pressure value.

Further, it is also possible to provide a flow meter or a flow velocity meter at the inlet side and the outlet side or only at the outlet side of the secondary diesel particulate filter for measuring the differential pressure. With such a construction, the differential pressure is obtained from the reading value of the flow meters or flow velocity meters provided at the inlet side and the outlet side of the secondary diesel particulate filter. Alternatively, the differential pressure may be obtained from the reading value of the flow meter, the flow velocity meter, or the like, at the outlet side of the secondary diesel particulate filter, by comparing the reading value for the initial state (the state immediately after regeneration) and the reading value for the state where there is caused deposition of the particulate matter in the secondary diesel particulate filter.

The embodiment of the present invention has the feature of obtaining the amount of the particulate matter deposited in the primary diesel particulate filter (DPF) 22 from the differential pressure obtained for the secondary diesel particulate filter 22A by using Equations (1) to (4), and thus, any instruments including those that are used conventionally for measuring a differential pressure may be used for measuring the differential pressure of the secondary diesel particulate filter.

Second Embodiment

Figure 8:
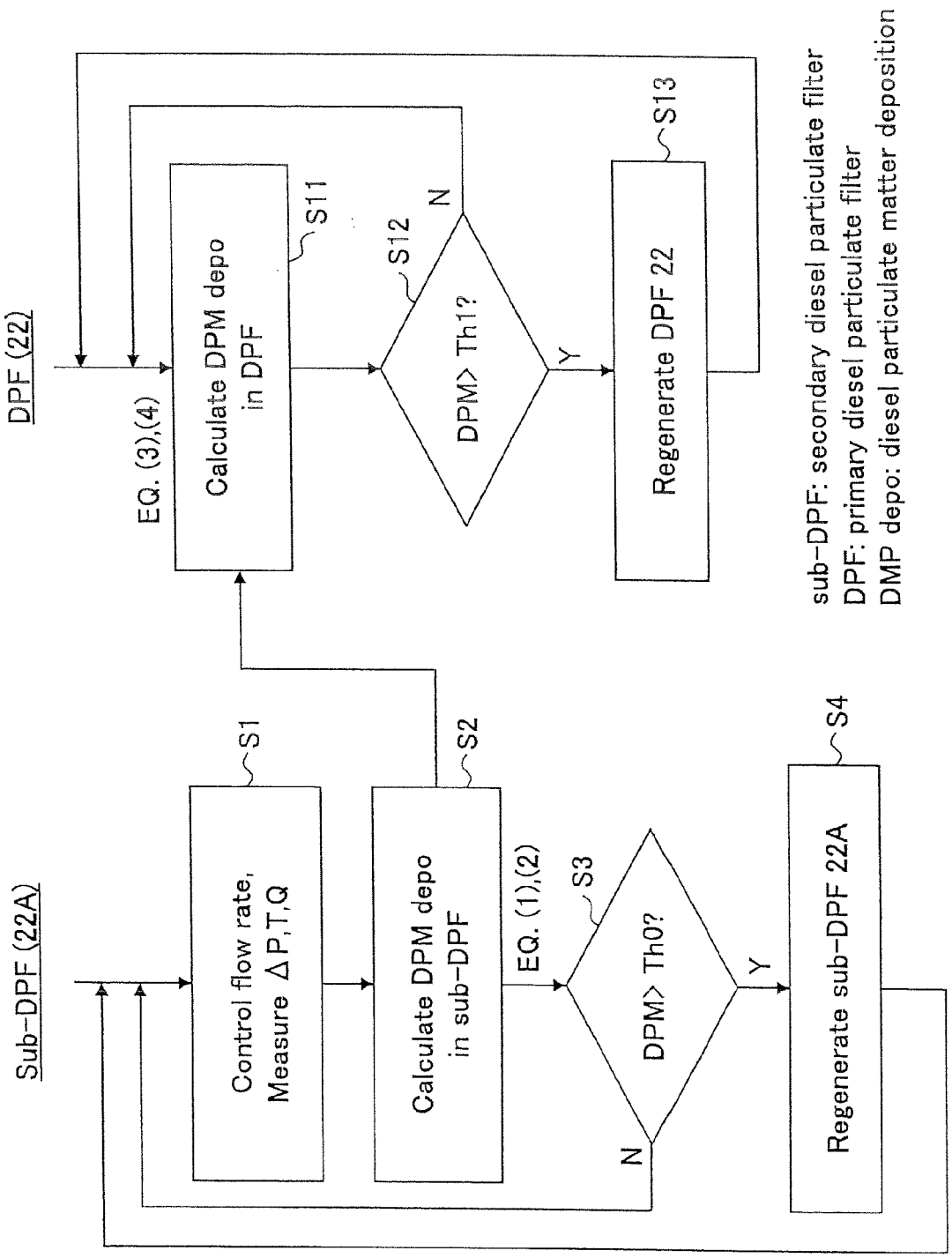
FIG. 8 is a flow chart explaining the regeneration operation of the diesel particulate filter in the exhaust gas purifying apparatus according to a second embodiment of the present invention.

FIG. 8 is a flowchart showing the exhaust gas purifying method according to a second embodiment of the present invention that uses the exhaust gas purifying apparatus of the embodiment of FIG. 4.

Referring to FIG. 8, the exhaust gas flow rate Q is detected by the flow meter 24 in step S1 and the differential pressure ΔP across the secondary diesel particulate filter 22A is detected by the differential pressure measuring part 22B. Further, the temperature of the exhaust gas is detected by using the temperature measuring part T1.

Next, in step S2, the layer thickness W of the particulate matter collected by the secondary diesel particulate filter 22A is obtained from the differential pressure ΔP detected in step S1 according to Equation (1). Here, it should be noted that the temperature T of the exhaust gas may be obtained by using the temperature measuring part T2 of the primary diesel particulate filter (DPF) 22 in place of using the temperature measuring part T1 of the secondary diesel particulate filter 22A as in the present case. Further, the temperature T may be calculated from the temperatures of the temperature measuring parts T1 and T2 (in the form of average value, maximum value, minimum value, for example). From the viewpoint of calculating the amount of the particulate matter more precisely, it is preferable to use the temperature measuring part T1 of the secondary diesel particulate filter 22A. For the thermometer, a thermocouple may be used, while it is also possible to use anything as long as it can measure the temperature. While it is preferable to measure the temperature of the exhaust gas inside the exhaust pipe, it is also possible to measure the temperature of the filter or the cell.

Further, in step S2, the mass $m_{soot}$ of the particulate matter collected by the cell 21b is obtained from the layer thickness W detected in step S1 by using Equation (2) mentioned previously.

Further, in step S3, it is judged whether or not the mass $m_{soot}$ of the layered particulate matter deposited in the cell 22b of the secondary diesel particulate filter 22A has exceeded a predetermined threshold Th0, and if the result is NO, the process returns to step S1.

When the mass $m_{soot}$ of the layered particulate matter deposited in the cell 22b of the secondary diesel particulate filter 22A has exceeded the predetermined threshold Th0 in step S3, the heater 22h is activated in step S4 and the particulate matter 22c is removed by burning.

Meanwhile, in the process of FIG. 8, the concentration PM of the particulate matter in the exhaust gas is obtained in step S11 from Equation (3) while using the mass $m_{soot}$ of the collected particulate matter in the cell 22b obtained in step S2, and the deposited amount $PM_{enter\,full\,filter}$ of the particulate deposited in the principal diesel particulate filter 22 is obtained from Equation (4) and from the collection efficiency of the primary diesel particulate filter (DPF) 22.

Thus, in step S12, it is judged whether or not the deposited amount $PM_{enter\,full\,filter}$ of the particulate matter in the primary diesel particulate filter (DPF) 22 exceeds a predetermined threshold value Th1, and if the result of judgment is NO, the operation returns to step S11.

In the event it is judged in step S12 that the deposited amount $PM_{enter\,full\,filter}$ of the particulate matter in the primary diesel particulate filter (DPF) 22 exceeds the predetermined threshold value Th1, post injection is executed in step S13 by controlling an engine control unit (ECU), and the deposited particulate matter in the primary diesel particulate filter (DPF) 22 is removed by burning. Thereby, regeneration of filter is achieved.

With the process of FIG. 8, it is possible to carry out the regeneration of the secondary diesel particulate filter 22A and the primary diesel particulate filter (DPF) 22 independently, and thus, it is possible to always maintain the deposited amount of the particulate matter 22c, or the amount of the soot layer, in the cell 22b, which constitutes the secondary diesel particulate filter 22A, to be a small value of about 0.5 g/l or less. With such a construction, it becomes possible to improve the sensitivity of the particulate matter sensor that uses the secondary diesel particulate filter 22A.

With the construction of the embodiment of FIG. 4, in which the valve 23 is inserted into the secondary exhaust line 21A, there is caused no such situation that the exhaust gas flows predominantly through the secondary diesel particulate filter where regeneration has been made even when the regeneration of the secondary diesel particulate filter 22A is conducted independently to the primary diesel particulate filter (DPF) 22, and there is caused no error in the evaluation of the deposited amount of the particulate matter in the primary diesel particulate filter (DPF) 22.

Thereby, it should be noted that there is no need for the valve 23 to maintain the exhaust gas flow rate in the secondary exhaust line 21A exactly at a constant level but it is just sufficient to avoid extreme deviation of the exhaust gas flow to the secondary exhaust line 21A.

Thus, in the second embodiment noted above, the differential pressure ΔP, the exhaust gas temperature T and the exhaust gas flow rate Q are measured (step S1), the mass of the particulate matter collected by the secondary diesel particulate filter is obtained by using Equations (1) and (2) from the foregoing result of measurement (step S2), and the amount of the particulate matter collected by the primary diesel particulate filter is obtained from the amount of the particulate matter collected in the secondary diesel particulate filter by using Equations (3) and (4) and further using the collection efficiency of the primary diesel particulate filter (step S11).

In FIG. 8, and also in FIG. 9 to be explained below, the primary diesel particulate filter (DPF) 22 is designated as DPF while the secondary diesel particulate filter 22A is designated as sub-DPF. Further, the deposition of diesel particulate matter is designated as DPM depo.

Figure 9:
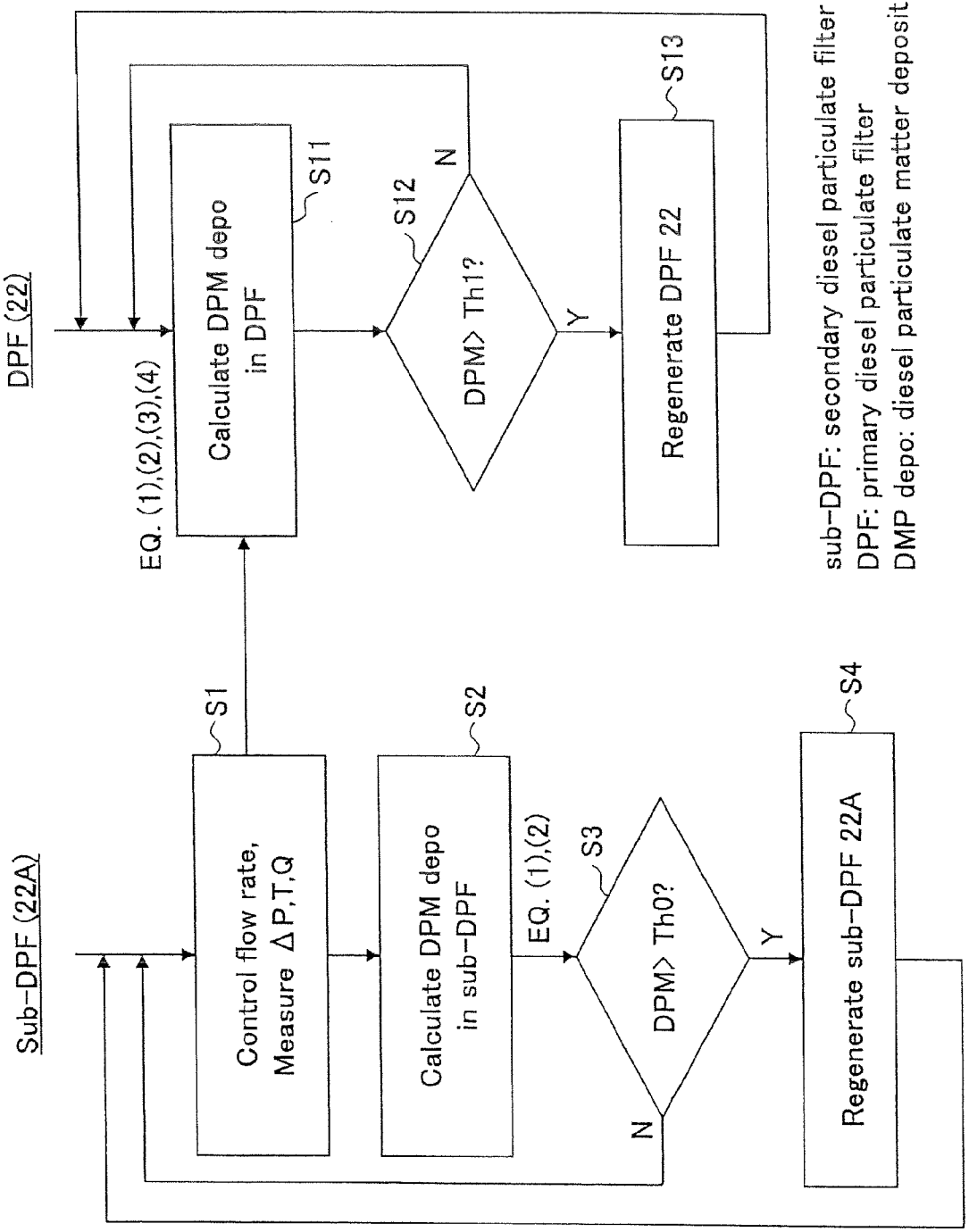
FIG. 9 is a flowchart explaining another regeneration operation of the diesel particulate filter of the exhaust gas purifying apparatus according to the second embodiment of the present invention.

On the other hand, the process of obtaining the amount of the particulate matter collected in the primary diesel particulate filter may be modified as shown in FIG. 9.

Figure 11:
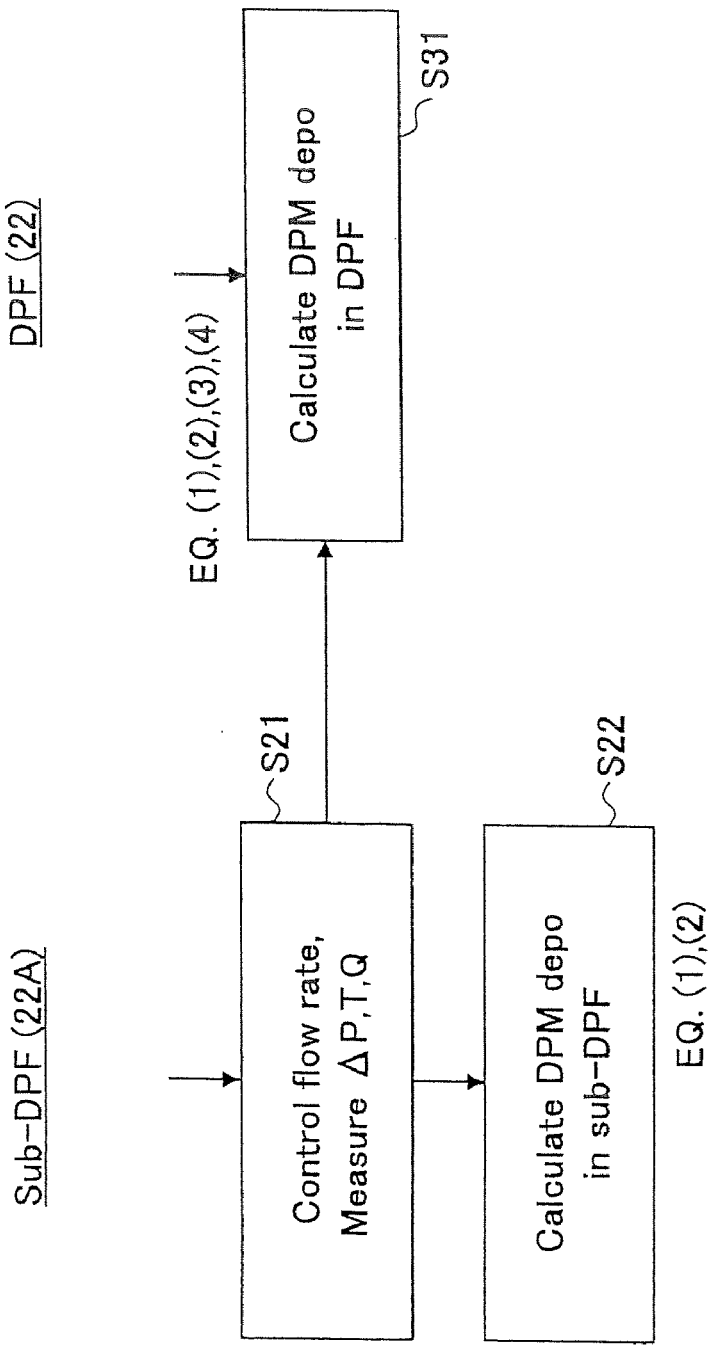
FIG. 11 is a flowchart showing a modification of the particulate matter measuring method of FIG. 10.

Thus, in FIG. 11, the process for obtaining the amount of the particulate matter collected by the primary diesel particulate filter (step S11) is carried out in parallel with the process of obtaining the amount of the particulate matter collected by the secondary diesel particulate filter (step S2), while using the result of measurement obtained in step S1.

Third Embodiment

Figure 10:
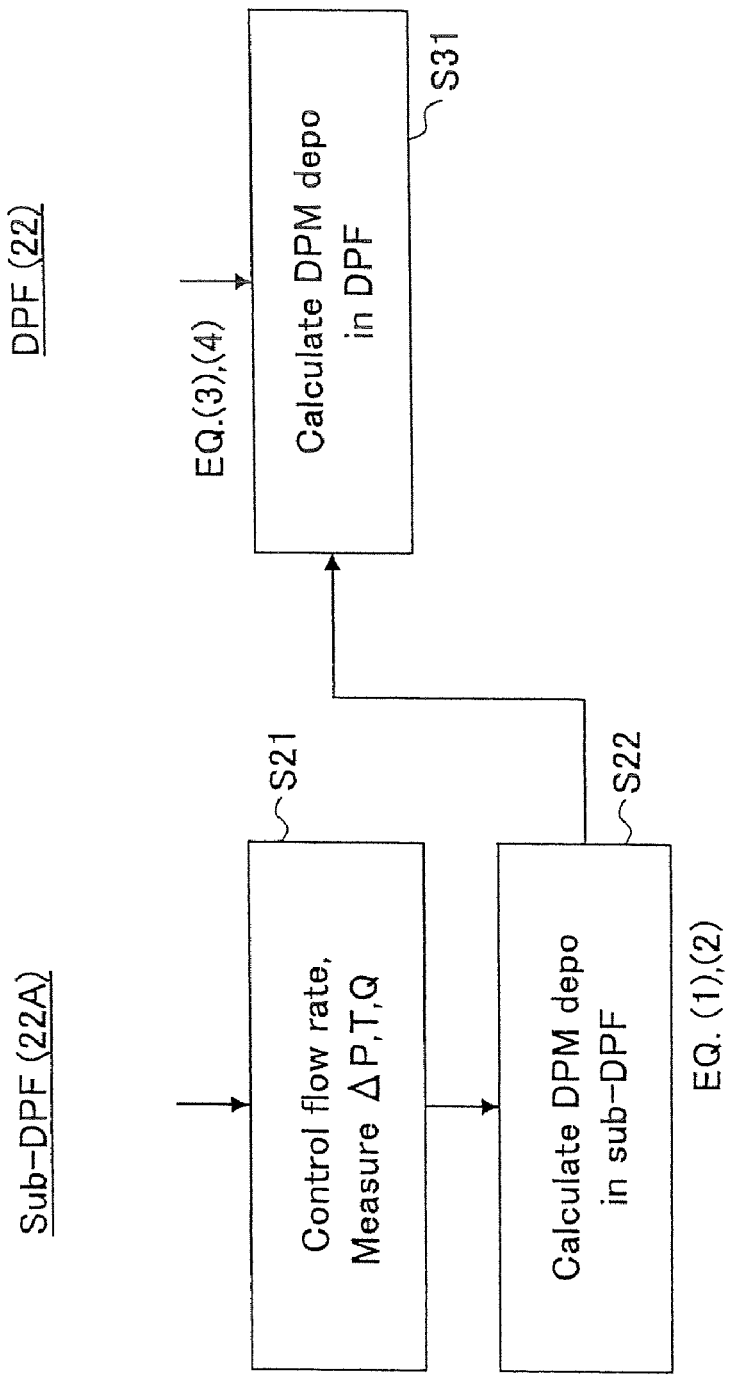
FIG. 10 is a flowchart showing the particulate matter measuring method according to a third embodiment of the present invention.

FIG. 10 is a flowchart showing the particulate matter measuring method according to a third embodiment of the present invention that uses the particulate matter sensor of the embodiment of FIG. 4, wherein those parts corresponding to the parts described previously are designated by the same reference numerals and the description thereof will be omitted.

Referring to FIG. 10, the flow rate in the secondary exhaust line 21A is set to a predetermined value in the range of about 50 to about 6000 ml/min in step S21 corresponding to the foregoing step S1 by using the flow meter 24, or in some cases by using the valve 23, and the differential pressure ΔP across the secondary diesel particulate filter 22A is detected by the differential pressure measuring part 22B. Further, the temperature of the exhaust gas is detected by using the temperature measuring part T1.

Next, in step S22 corresponding to the foregoing step S2, the layer thickness W of the particulate matter collected by the secondary diesel particulate filter 22A is obtained from the differential pressure ΔP detected in step S1 according to Equation (1). Here, it should be noted that the temperature T of the exhaust gas may be obtained by using the temperature measuring part T2 of the primary diesel particulate filter (DPF) 22 in place of using the temperature measuring part T1 of the secondary diesel particulate filter 22A as in the present example. Further, the temperature T may be calculated from the temperatures of the temperature measuring parts T1 and T2 (in the form of average value, maximum value, minimum value, for example). From the viewpoint of calculating the amount of the particulate matter more precisely, it is preferable to use the temperature measuring part T1 of the secondary diesel particulate filter 22A. For the temperature measuring part, a thermocouple may be used, while it is also possible to use anything as long as it can measure the temperature. While it is preferable to measure the temperature of the exhaust gas inside the exhaust pipe, it is also possible to measure the temperature of the filter or the cell.

Further, in step S22, the mass $m_{soot}$ of the particulate matter collected by the cell 21b is obtained from the layer thickness W detected in step S1 by using Equation (2) mentioned previously.

Further, in the process of FIG. 10, the concentration PM of the particulate matter in the exhaust gas is obtained in step S31 corresponding to the foregoing step S11 from Equation (3) while using the mass $m_{soot}$ of the collected particulate matter in the cell 22b obtained in step S22, and the deposited amount $PM_{enter\ full\ filter}$ of the particulate deposited in the principal diesel particulate filter 22 is obtained from Equation (4) and from the collection efficiency of the primary diesel particulate filter (DPF) 22.

Thus, in the third embodiment noted above, the differential pressure ΔP, the exhaust gas temperature T and the exhaust gas flow rate Q are measured (step S21), the mass of the particulate matter collected by the secondary diesel particulate filter is obtained by using Equations (1) and (2) from the foregoing result of measurement (step S22), and the amount of the particulate matter collected by the primary diesel particulate filter is obtained from the amount of the particulate matter collected in the secondary diesel particulate filter by using Equations (3) and (4) and further using the collection efficiency of the primary diesel particulate filter (step S31).

In FIG. 10, and also in FIG. 13 to be explained below, the primary diesel particulate filter (DPF) 22 is designated as DPF while the secondary diesel particulate filter 22A is designated as sub-DPF. Further, the deposition of diesel particulate matter is designated as DPM depo.

On the other hand, the process of obtaining the amount of the particulate matter collected in the primary diesel particulate filter may be modified as shown in FIG. 11.

Thus, in FIG. 11, the process for obtaining the amount of the particulate matter collected by the primary diesel particulate filter (step S31) is carried out in parallel with the process of obtaining the amount of the particulate matter collected by the secondary diesel particulate filter (step S22), while using the result of measurement obtained in step S21.

Fourth Embodiment

Figure 12:
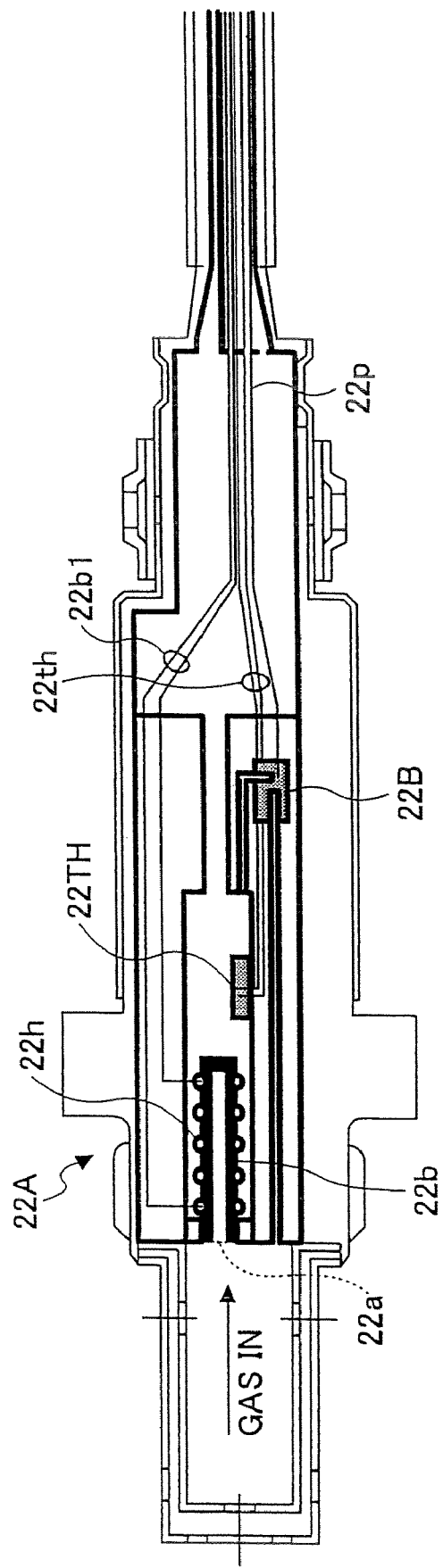
FIG. 12 is a diagram showing the construction of a particulate matter sensor according to a third embodiment of the present invention.

FIG. 12 shows the construction of a particulate matter sensor according to a fourth embodiment of the present invention, wherein those parts corresponding to the parts described previously are designated by the same reference numerals and the description thereof will be omitted.

With the embodiment of FIG. 12, there is further provided a thermistor 22Th outside the housing of the particulate matter detection sensor as a temperature measuring part, wherein a resistance value of the thermistor 22Th is read by a control circuit via a signal line 22th.

With the embodiment of FIG. 12, the thermistor 22Th is integrated into the housing of the particulate sensor, and as a result, it becomes possible to construct the particulate matter sensor in a compact size, suitable for providing at any desired location of the exhaust line of the diesel engine.

Fifth Embodiment

Figure 13:
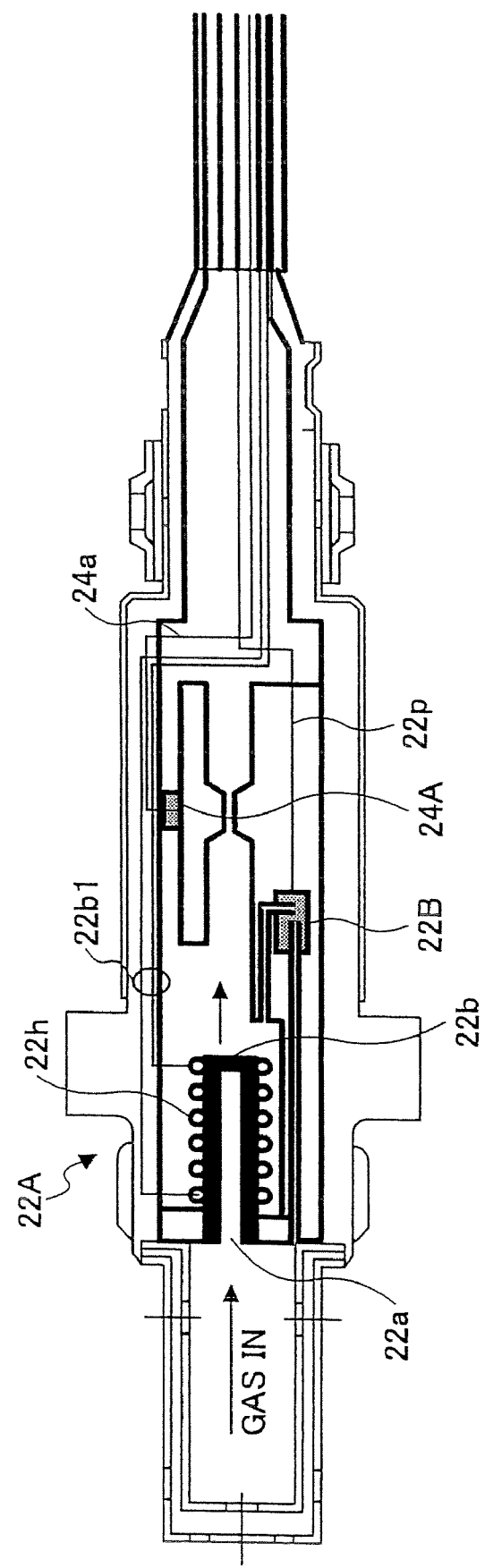
FIG. 13 is a diagram showing the construction of a particulate matter sensor according to a fourth embodiment of the present invention.

FIG. 13 shows the construction of a particulate matter sensor according to a fifth embodiment of the present invention, wherein those parts corresponding to the parts described previously are designated by the same reference numerals and the description thereof will be omitted.

With the embodiment of FIG. 13, there is provided a flow meter 24A of a differential-pressure venturi tube inside the housing of the particulate matter sensor as the flow meter 24, wherein the output of the flow meter 24A is forwarded to the control circuit via a signal line 24a.

Thus, with the embodiment of FIG. 13, it becomes possible to read the flow rate of the exhaust gas flowing through the cell 22b by the flow meter 24A of the differential-pressure venturi tube. Because the flow meter 24A is integrated into the housing of the particulate matter sensor, the particulate matter sensor is constructed to have a compact size, and it becomes possible to provide the particulate matter sensor at any desired location of the exhaust line of the diesel engine.

Figure 14:
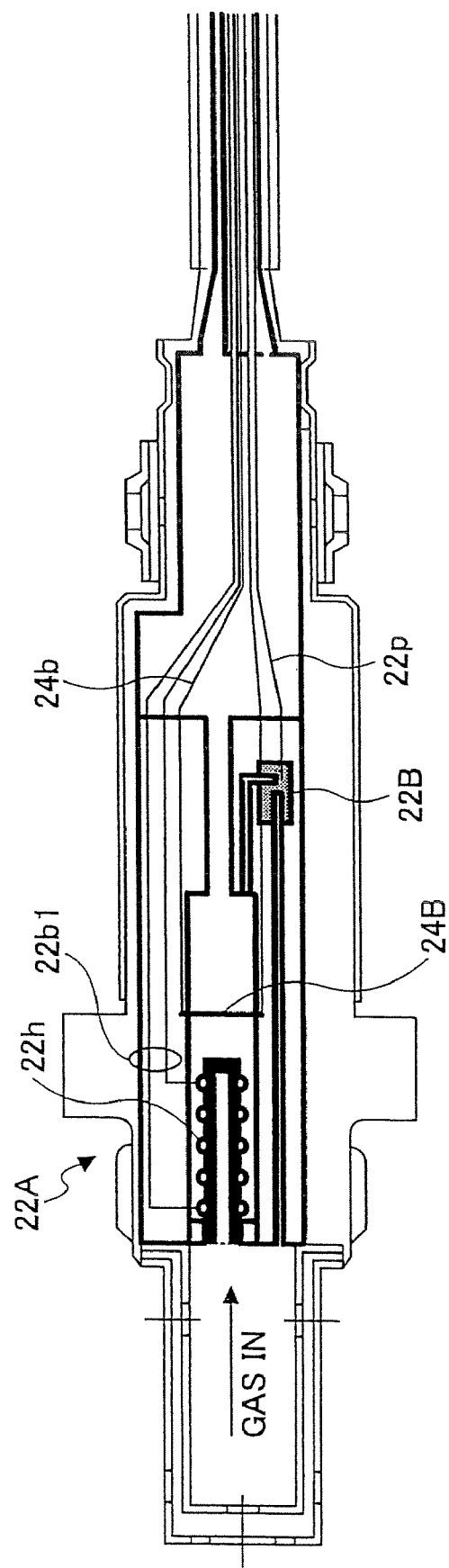
FIG. 14 is a diagram showing the construction of a particulate matter detection sensor according to a modification of FIG. 13.

FIG. 14 shows a modification of the particulate sensor of FIG. 13.

Referring to FIG. 14, there is provided a simple hot-wire flow meter 24B with the present embodiment in place of the flow meter 24A of differential-pressure venturi tube of FIG. 13, and the flow rate of the exhaust gas flowing through the cell 22b is read by the control circuit via a signal line 24b.

Further, while the explanation heretofore has been made for the case of using a honeycomb component of SiC for the primary diesel particulate filter (DPF) 22 and the secondary diesel particulate filter 22A, the embodiment of the present invention is by no means limited to such particular filter components, and it is also possible to use a composite material containing silicon carbide by about 60% or more, such as a composite of silicon carbide and metal such as silicon (the embodiment of the present invention includes such a composite also in silicon carbide), a nitride such as aluminum nitride, silicon nitride, boron nitride, tungsten nitride, or the like, a carbide such as zirconium carbide, titanium carbide, tantalum carbide, tungsten carbide, or the like, an oxide such as alumina, zirconium oxide, cordierite, mullite, silica, aluminum titanate, or a porous body of metal such as stainless steel. Further, it is possible to use a structural body such as corrugate or element plate in addition to the honeycomb structure.

The exhaust gas purifying apparatus by using the particulate matter sensor of the embodiment of the present invention has a compact size and is applicable not only to large vehicles such as trucks or industrial machines but also to passenger cars.

Obviously, numerous modifications and variations of the present invention are possible in light of the above teachings. It is therefore to be understood that within the scope of the appended claims, the invention may be practiced otherwise than as specifically described herein.

What is claimed is:

1. A particulate matter detection sensor for detecting particulate matter in an exhaust line on which a diesel particulate filter is provided, comprising:
   a secondary exhaust line configured to be connected to the exhaust line, said secondary exhaust line branching out a flow of an exhaust gas from said exhaust line;
   a flow control valve provided to the secondary exhaust line;
   a particulate matter detection filter provided to said secondary exhaust line and having a volumetric soot storage capacity smaller than the volumetric soot storage capacity of the diesel particulate filter; and
   a differential pressure measuring part configured to measure a differential pressure between an inlet and an outlet of said particulate matter detection filter,
   wherein said particulate matter detection sensor is configured to detect an amount of particulate matter in said exhaust line based on said differential pressure measured by said differential pressure measuring part.

2. The particulate matter detection sensor as claimed in claim 1, further comprising a flow meter.

3. The particulate matter detection sensor as claimed in claim 2, further comprising a temperature measuring part.

4. The particulate matter detection sensor as claimed in claim 2, further comprising a heater.

5. The particulate matter detection sensor as claimed in claim 2, further comprising a vessel, wherein at least one of said particulate matter detection filter, said differential pressure measuring part, a temperature measuring part or said flow meter is accommodated in said vessel.

6. The particulate matter detection sensor as claimed in claim 2, wherein said particulate detection filter comprises any of SiC, aluminum nitride, silicon carbide, boron nitride, tungsten nitride, zirconium carbide, titanium carbide, tantalum carbide, tungsten carbide, alumina, zirconium oxide, cordierite, mullite, silica, or aluminum titanate.

7. The particulate matter detection sensor as claimed in claim 2, wherein said flow control valve is used to maintain a constant flow rate of the exhaust gas in the secondary exhaust line based on measurements made by said flow meter.

8. The particulate matter detection sensor as claimed in claim 1, further comprising a temperature measuring part.

9. The particulate matter detection sensor as claimed in claim 8, further comprising a heater.

10. The particulate matter detection sensor as claimed in claim 8, further comprising a vessel, wherein at least one of said particulate matter detection filter, said differential pressure measuring part, said temperature measuring part or a flow meter is accommodated in said vessel.

11. The particulate matter detection sensor as claimed in claim 8, wherein said particulate detection filter comprises any of SiC, aluminum nitride, silicon carbide, boron nitride, tungsten nitride, zirconium carbide, titanium carbide, tantalum carbide, tungsten carbide, alumina, zirconium oxide, cordierite, mullite, silica, or aluminum titanate.

12. The particulate matter detection sensor as claimed in claim 1, further comprising a heater.

13. The particulate matter detection sensor as claimed in claim 12, further comprising a vessel, wherein at least one of said particulate matter detection filter, said differential pressure measuring part, a temperature measuring part or a flow meter is accommodated in said vessel.

14. The particulate matter detection sensor as claimed in claim 12, wherein said particulate detection filter comprises any of SiC, aluminum nitride, silicon carbide, boron nitride, tungsten nitride, zirconium carbide, titanium carbide, tantalum carbide, tungsten carbide, alumina, zirconium oxide, cordierite, mullite, silica, or aluminum titanate.

15. The particulate matter detection sensor as claimed in claim 1, further comprising a vessel, wherein at least one of said particulate matter detection filter, said differential pressure measuring part, a temperature measuring part or a flow meter is accommodated in said vessel.

16. The particulate matter detection sensor as claimed in claim 15, wherein said particulate detection filter comprises any of SiC, aluminum nitride, silicon carbide, boron nitride, tungsten nitride, zirconium carbide, titanium carbide, tantalum carbide, tungsten carbide, alumina, zirconium oxide, cordierite, mullite, silica, or aluminum titanate.

17. The particulate matter detection sensor as claimed in claim 1, wherein said particulate detection filter comprises any of SiC, aluminum nitride, silicon carbide, boron nitride, tungsten nitride, zirconium carbide, titanium carbide, tantalum carbide, tungsten carbide, alumina, zirconium oxide, cordierite, mullite, silica, or aluminum titanate.

18. The particulate matter detection sensor as claimed in claim 1, wherein said flow control valve is located downstream of said particulate matter detection filter.

19. The particulate matter detection sensor as claimed in claim 18, wherein said flow control valve is used to maintain a constant flow rate of the exhaust gas in the secondary exhaust line.

* * * * *